(12) United States Patent
Afnan et al.

(10) Patent No.: US 6,874,928 B2
(45) Date of Patent: Apr. 5, 2005

(54) MIXING APPARATUS AND METHOD

(75) Inventors: Ali Mohammad Afnan, Northwich (GB); Robert Symes Chisholm, Frodsham (GB)

(73) Assignee: Astra Zeneca U.K. Limited, London (GB)

( * ) Notice: Subject to any disclaimer, the term of this patent is extended or adjusted under 35 U.S.C. 154(b) by 0 days.

(21) Appl. No.: 10/790,703

(22) Filed: Mar. 3, 2004

(65) Prior Publication Data

US 2004/0165475 A1 Aug. 26, 2004

Related U.S. Application Data

(63) Continuation of application No. 10/337,983, filed on Jan. 8, 2003, now Pat. No. 6,776,517, which is a continuation of application No. 09/784,081, filed on Feb. 16, 2001, now Pat. No. 6,517,230.
(60) Provisional application No. 60/186,759, filed on Mar. 3, 2000.

(30) Foreign Application Priority Data

Feb. 17, 2000 (GB) ............................................. 0003641

(51) Int. Cl.⁷ .................................................. B01F 9/00
(52) U.S. Cl. ...................... 366/142; 366/143; 366/200; 366/208; 366/213; 366/219; 366/220
(58) Field of Search ................................ 366/140, 143, 366/197, 200, 208, 209, 210, 213, 218, 219, 220, 237, 239, 241, 142; 73/32 R

(56) References Cited

U.S. PATENT DOCUMENTS 511,040 A 12/1893 Braden
586,280 A 7/1897 Argerbright
1,511,386 A 10/1924 Wildberger (Continued)

FOREIGN PATENT DOCUMENTS

| CA | 2398068 | 8/2001 |
|----|---------|--------|
| DE | 3337 403 A1 | 5/1985 |
| EP | 0 631 810 A1 | 1/1995 |
| EP | 0 801 299 A1 | 10/1997 |
| FR | 2 703 153 | 9/1994 |
| GB | 1005151 | 9/1965 |
| WO | WO 00/07705 | 2/2000 |
| WO | WO 01/60503 | 8/2001 |

OTHER PUBLICATIONS

Patent Abstracts of Japan, vol. 1995, No. 03, Apr. 28, 1995 & JP 06331542 A (Minamide Syst Eng–KK), Dec. 2, 1994 Abstract.

Wang et al. "Acousto–Optic Tunable Filters Spectrally Modulate Light", *Laser Focus World*, Aug. 1994.

*Primary Examiner*—Tony G. Soohoo
(74) *Attorney, Agent, or Firm*—Mayer Brown Rowe & Maw LLP

(57) ABSTRACT

Apparatus for mixing a number of components comprising a vessel for receiving the components, drive means for rotating or oscillating the vessel about an axis to effect mixing of the components within the vessel, and at least one spectroscopic monitoring means for repeatedly scanning the mixture to obtain data for use in monitoring changes in the spectroscopic profile of the mixture as mixing proceeds, the monitoring means by mounted off-axis relative to the axis about which the vessel is rotatable or oscillatable.

28 Claims, 6 Drawing Sheets

U.S. PATENT DOCUMENTS

| | | |
|---|---|---|
| 2,514,126 A | 7/1950 | Fischer |
| 3,137,327 A | 6/1964 | Muench |
| 3,224,741 A | 12/1965 | Muench, Sr. |
| 3,540,700 A | 11/1970 | Freedman |
| 3,749,370 A | 7/1973 | Clech et al. |
| 3,997,786 A | 12/1976 | Lauer et al. |
| 4,042,221 A | 8/1977 | Myers et al. |
| 4,283,148 A | 8/1981 | Peterson |
| 4,332,479 A | 6/1982 | Crocker et al. |
| 4,571,089 A | 2/1986 | Gudlauski et al. |
| 4,676,658 A | 6/1987 | Herfeld |
| 4,698,917 A | 10/1987 | Debolini |
| 4,704,035 A | 11/1987 | Kowalczyk |
| 4,820,045 A | 4/1989 | Boisde |
| 4,957,373 A | 9/1990 | Derksen et al. |
| 5,054,933 A | 10/1991 | Derksen et al. |
| 5,504,332 A | 4/1996 | Richmond et al. |
| 5,516,207 A | 5/1996 | Haicht |
| 5,890,803 A | 4/1999 | Jolink |
| 5,924,311 A | 7/1999 | Matsuda et al. |
| 5,946,088 A | 8/1999 | Aldridge |
| 6,244,118 B1 | 6/2001 | Andersson et al. |
| 6,490,035 B1 | 12/2002 | Folestad et al. |
| 6,517,230 B1 | 2/2003 | Afnan et al. |
| 6,595,678 B2 | 7/2003 | Folestad et al. |

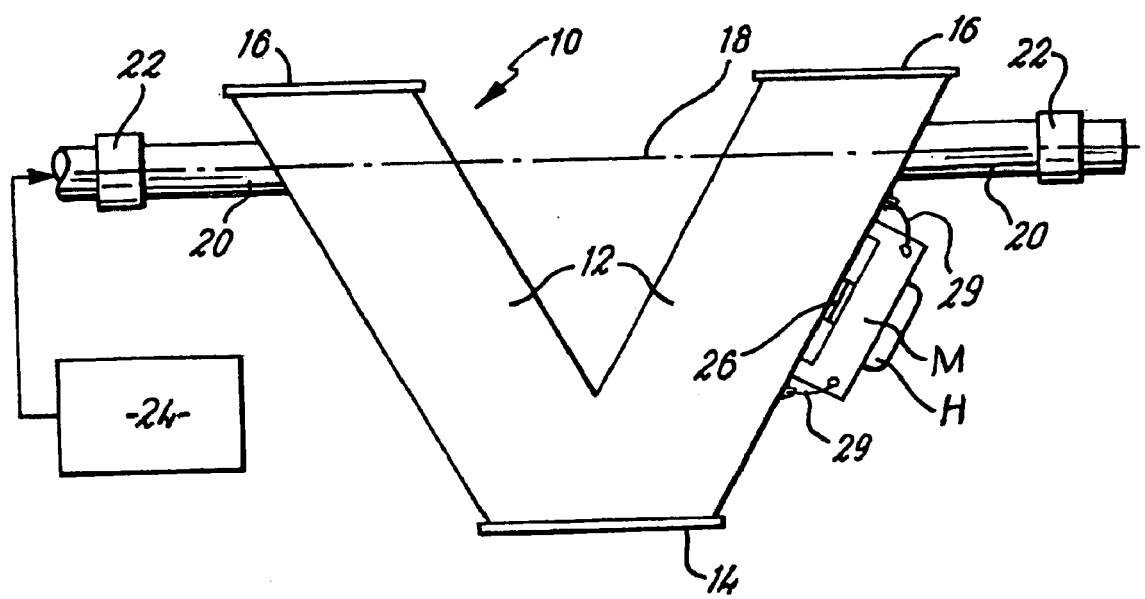
FIG. 1
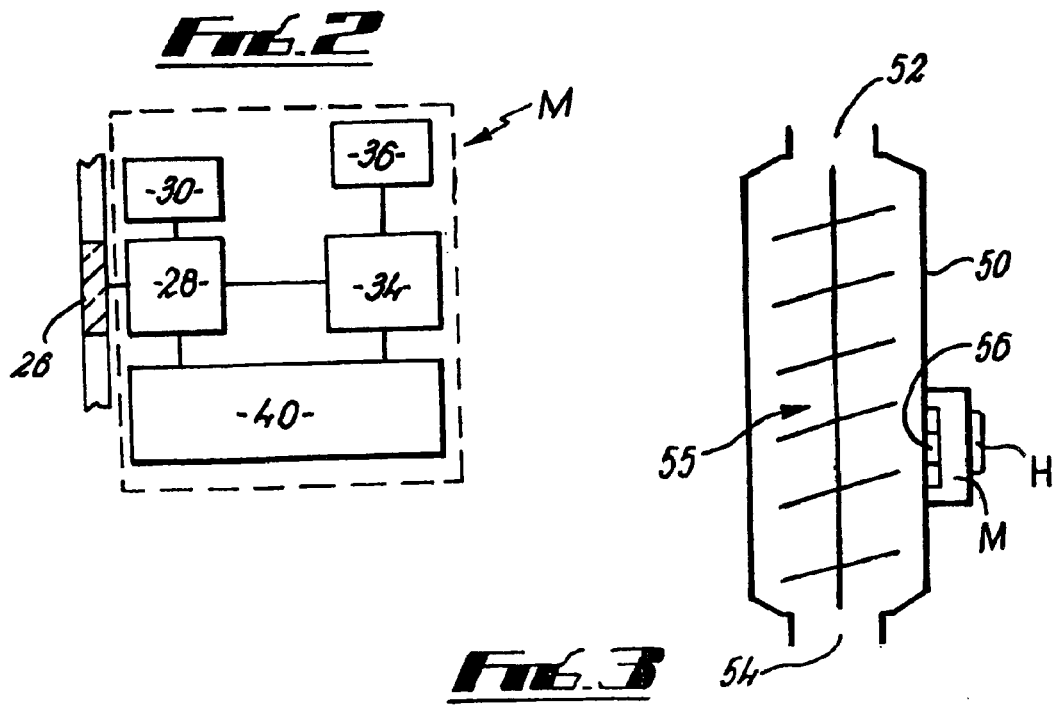
FIG. 2
FIG. 3

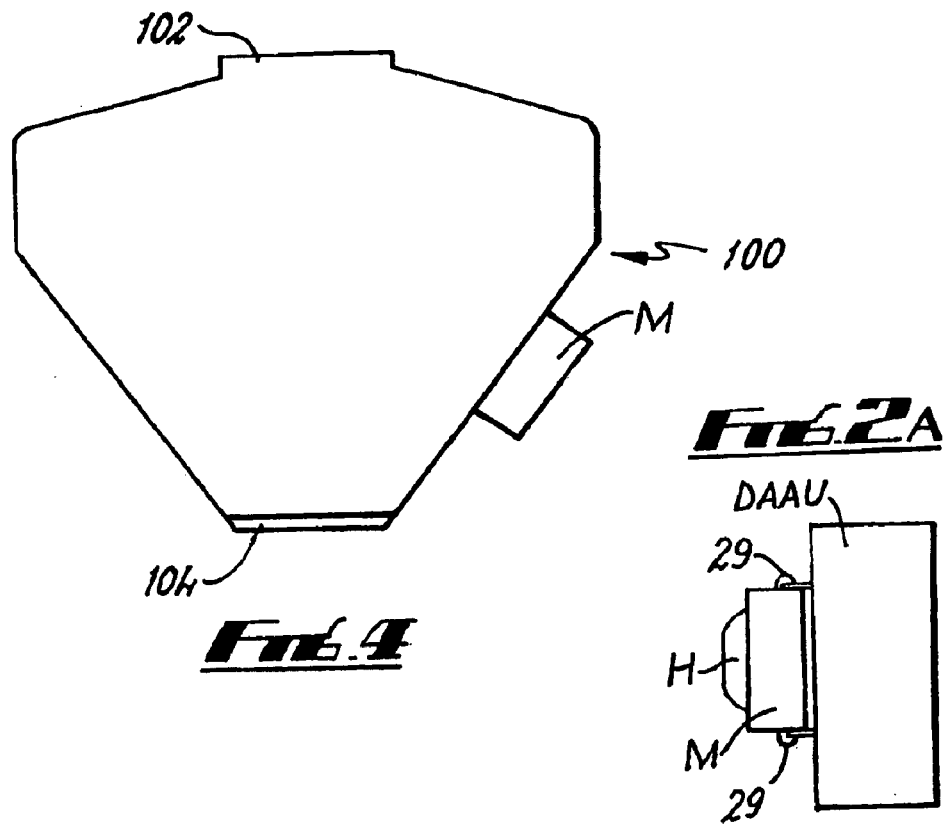
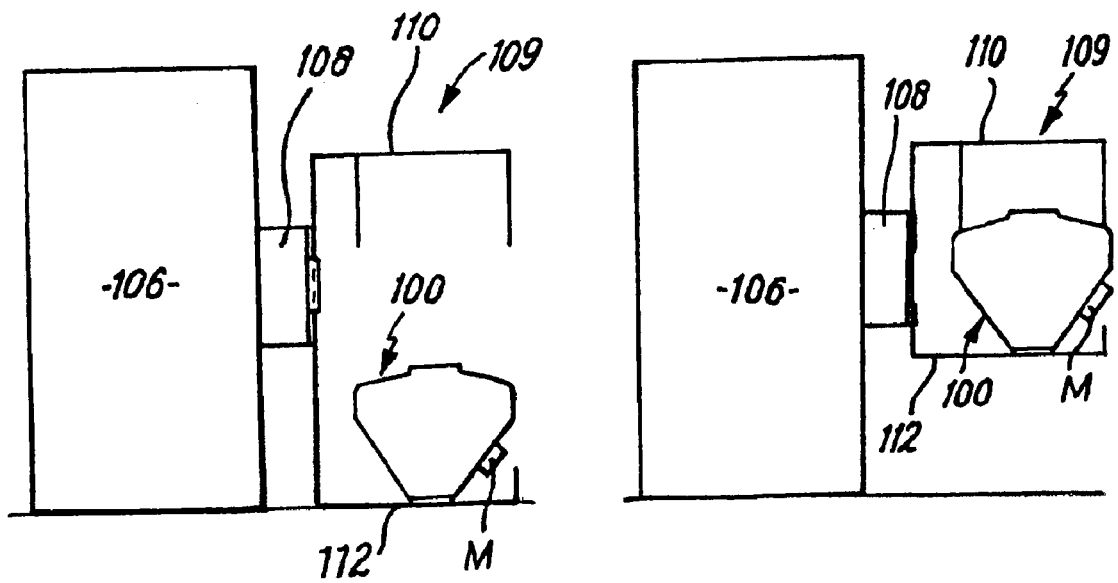

MIXING APPARATUS AND METHOD

CROSS REFERENCE TO RELATED APPLICATIONS

This application is continuation of U.S. Ser. No. 10/337,983, filed Jan. 8, 2003 now U.S. Pat. No. 6,776,517, which further is a continuation of U.S. Ser. No. 09/784,081, filed Feb. 16, 2001, now U.S. Pat. No. 6,517,230, issued Feb. 11, 2003, and which further claims priority from U.S. Provisional Ser. No. 60/186,759, filed Mar. 3, 2000. These applications, in their entirety, are incorporated herein by reference.

This invention relates to apparatus for and a method of mixing components, for example to effect blending of components to form a homogeneous mixture. The components will usually be in the form of powders but the invention is also applicable to the mixing of other fluent components such as liquids. Typically the components to be mixed comprise pharmaceutical actives and excipients prior to further processing thereof, e.g. tableting.

The production of homogeneous mixtures of actives and excipients is of particular importance in the pharmaceutical industry.

EP-A-0631810 discloses that in-line monitoring of the degree of homogeneity achieved in the course of blending components such as pharmaceutical actives and excipients is possible by detecting the spectroscopic characteristics of the mixture during the blending process. Where the blending process is carried out by means of a rotating mixing vessel, EP-A-0631810 teaches that the device for projecting radiation into and receiving reflected radiation from the mixture is associated with a shaft about which the vessel, specifically a V-blender, is rotated. This arrangement results in the device being located invasively with respect to the interior of the mixing vessel. The reflected radiation is conveyed to spectroscopic means located in the vicinity of the rotating mixing vessel for storage and analysis by the spectroscopic means or by a separate data acquisition and a control computer linked to the spectroscopic means.

The present invention seeks to provide improved in-line spectroscopic monitoring of mixing, especially but not exclusively blending, processes which may be non-invasive while affording greater freedom in terms of siting relative to the mixing zone.

According to one aspect of the present invention there is provided apparatus for mixing a number of components comprising a vessel for receiving the components, drive means for rotating or oscillating the vessel about an axis to effect mixing of the components within the vessel, and at least one spectroscopic monitoring means for repeatedly scanning the mixture to obtain data for use in monitoring changes in the spectroscopic profile of the mixture as mixing proceeds, the monitoring means being mounted off-axis relative to the axis about which the vessel is rotatable or oscillatable.

The monitoring means may be provided directly on-board the vessel or may instead be provided indirectly on-board the vessel as a result of being provided at least in part on a structure which rotates or oscillates with the vessel. In the former case for instance, the monitoring means may be mounted on a wall of the vessel while in the latter case the monitoring means may be carried at least in part by a frame which supports the vessel and through the agency of which the vessel is rotated or oscillated. References herein to the monitoring means being directly or indirectly on-board the vessel are to construed as referring the foregoing possibilities.

The profiles derived from scanning (hereinafter the "scanned profiles") may be monitored for convergence towards a static condition. This may for example involve comparison with a predetermined target spectroscopic profile. In this context, it is to be understood that the initial spectra of the components before mixing will correspond generally to the spectrum of each of the components. As the mixing process proceeds, the spectra of the mixture will undergo change and begin to converge towards the spectra of the homogeneous mixture. Thus, the mixing process can be controlled with reference to the spectroscopic profile obtained by the monitoring means and, in particular, may be terminated when the scanned profiles meet a predetermined criterion, e.g. when the scanned profiles attain or converge towards a substantially static condition. This may for example be satisfied when the scanned profile substantially matches the target profile or when two or more scanned profiles (or parts thereof) of the mixture are substantially the same or differ from one another by no more than a pre-defined extent.

Where used, the target profile may be representative of a selected condition of the mixture; for instance, it may be representative of the homogeneous end-point for a mixture of the components undergoing blending or an intermediate state lying between the homogeneous end point and the unmixed state.

Often the components undergoing mixing will have different chemical compositions. However, the invention also encompasses the mixing of components having the same or substantially the same chemical composition. For example, the apparatus of the invention may be used for mixing components which have the same or substantially the same chemical composition but have differing physical characteristics, such as moisture content, particle distribution etc. Thus, one application of the invention lies in the combining of two fractions of the same material, one fraction comprising fines and the other comprising coarser particles, the mixing process being carried out to produce a mixture in which the fines are dispersed into the coarser particles, e.g. to secure a substantially uniform distribution of fines in the mixture.

Control means responsive to the monitoring means may be provided for controlling the mixing process.

Thus, the drive means may be controlled by the control means in dependence upon the result of the comparison so that the mixing process can be terminated when the profiles derived from scanning converge on or substantially match the predetermined profile or converge towards a static condition where the changes in scanned profiles (or parts thereof) are no greater than a predefined extent.

The monitoring means may include or be associated with comparison means for comparing spectroscopic profiles corresponding to the scanning-derived data with the target profile or previously derived scanned profiles obtained during a given mixing cycle. Thus, the monitoring means may embody the comparison means so that the comparison of scanned profiles with target profile or previously derived scanned profiles is effected during rotation or oscillation of the monitoring means with the vessel.

When the scanned profiles have converged to a predetermined extent towards a static condition (e.g. when a desired level of matching between the scanned profile and a target profile is obtained), the monitoring means may be arranged to supply an output signal to signal utilising means for controlling the mixing process. For instance, the signal utilising means may be operable in response to receiving the output signal to terminate the mixing process by suitable control of the drive means, e.g. by disabling the drive means and terminating rotary or angular movement of the vessel.

In an alternative embodiment, the comparison means may be separate from the monitoring means and the vessel. In this case, data transferring means will be provided for transferring scanning-derived data from the monitoring means to the comparison means. The data transferring means may for example comprise a signal transmitter directly or indirectly on-board the vessel and a receiver associated with the comparison means whereby the data is transmitted radiatively from the monitoring means to the comparison means.

Matching of the newly derived scanned and target or previously obtained scanning profiles (at least to the desired extent) conveniently leads to automatic termination of the mixing process. However, we do not exclude the possibility that such matching, whether carried out directly or indirectly on-board the vessel or elsewhere, may instead give rise to an output signal, e.g. visual or audible, suitable for attracting an operator's attention to the fact that mixing to an acceptable level, e.g. an acceptable level of homogeneity, has been secured and that the mixing process can be terminated and the mixture transferred to a subsequent processing stage.

The monitoring means is preferably self-powered and to this end conveniently includes a power source which may be in the form of one or more batteries, preferably rechargeable batteries.

Where comparison of the newly derived profiles and target or previously derived profiles is carried out directly or indirectly on-board the vessel, the monitoring means may include data storage means for storing the scanning-derived data, optinally together with at least one predetermined target profile where applicable. The scanning-derived data collected during the course of a mixing process may then, during or on completion of a mixing cycle, be transferred to separate data acquisition means to allow a record to be maintained for a series of mixing cycles.

The monitoring means conveniently includes a signal transmitter for transmitting signals radiatively to a receiver located in the vicinity of or remotely from the vessel thereby eliminating hard-wired connections (such as electrical conductors, optical fibres and the like) between the monitoring means and signal utilising means and/or a data acquisition means linked to the receiver. For instance, the transmitted signal may be in the form of a radiation signal such as a radio frequency signal.

In a preferred embodiment, the monitoring means comprises a self-contained unit capable of being battery-powered and is provided with means for detachably docking the unit with the vessel, preferably non-invasively, or with structure which rotates or oscillates with the vessel so that the scanning means is in registry with a window through which spectroscopic data is obtained.

Where the monitoring means is battery powered, the battery supply may form part of the self-contained unit or it may comprise a separate unit which may be provided directly or indirectly on-board the vessel. In this event, because the battery supply unit and the monitoring means both rotate or oscillate with the vessel, there may be a hard-wired connection between the two.

The self-contained unit will typically comprise at least the scanning means, a radiative signal transmitter, and optionally a compartment or compartments containing or for reception of a battery or batteries for powering the unit. In addition, the self-contained unit may include data storage means and said comparison means; for instance, the data storage means and the comparison means may both be embodied in a microprocessor or computer forming part of the unit.

The self-contained unit is conveniently docked with the vessel in registry with the window by means of releasable, preferably quick-release, devices, e.g. in the form of one or more latching devices co-operating with a keeper or keepers. The releasable devices are preferably arranged to clamp the unit securely to the vessel. One form of suitable device comprises a sprung draw latch commercially from Southco Europe Limited of Cheltenham, England.

Instead of being mounted for rotation or oscillation with the vessel, the monitoring means may be located at a fixed position, the arrangement being such that the monitoring means "views" the contents of the vessel at least during part of its cycle of rotation or oscillation. Thus, for example, the vessel may be provided with a window through which monitoring means "views" the contents of the vessel as the window traverses the line of sight of the monitoring means. The window may be strategically located at that part of the vessel which makes the closest approach to the monitoring means during each cycle of rotation or oscillation of the vessel and the window may be of elongated configuration in the direction of travel past the monitoring means so as to afford an extended interval of "viewing".

The monitoring means may be operable at only predetermined points during each cycle of rotation or oscillation of the vessel.

Means may be provided to sense the angular position of the vessel with respect to a datum position and, if desired, control operation of the monitoring means so that data relating to the mixture is only collected at said predetermined points. The monitoring means may be disabled at other times. Such predetermined points may for instance correspond to points during said cycle when the mixture can be expected to be in contact with the wall of the vessel at the location "viewed" by the monitoring means.

A preferred alternative however is to arrange the monitoring means to collect data substantially continuously throughout the cycle of rotation or oscillation (e.g. at the rate of one scan per second) and, from the data collected, discriminate between data corresponding to the points in the cycle when the mixture makes suitable contact with the window, i.e. data representative and data unrepresentative of the state of mixing. In this case, it may not be necessary to provide means for determining the angular position of the vessel.

Particularly but not necessarily exclusively where the monitoring means is fixed relative to the moving vessel, the vessel may, with respect to the radiation used for monitoring, be substantially transparent over an extended or substantially the entire area thereof.

The walls of the vessel may be fabricated at least in part, e.g. at least a major part and possibly substantially entirely, from a plastics material. The plastics material may be one which is transparent with respect to the radiation used (e.g. near infra red radiation).

While the vessel will normally comprise a rigid structure, usually of metal such as stainless steel, we do not exclude the possibility of the vessel being constituted by a flexible bag, e.g. of a plastics material. The bag and monitoring means may be adapted to enable the monitoring means to be coupled to the bag or the monitoring means may be mounted separately from the bag either in fixed relation to the bag or on a structure that rotates or oscillates with the bag, as described above.

Various other aspects of the invention are indicated below which other aspects may, where the context admits, be combined with each other and/or with said one aspect and/or any of the other features defined above.

According to a second aspect of the present invention there is provided apparatus for mixing a number of components (for example to produce a homogeneous mixture), comprising a vessel for receiving the components, drive means for rotating or oscillating the vessel about an axis to effect mixing of the components within the vessel, and at least one spectroscopic monitoring means provided directly or indirectly on-board the vessel for repeatedly scanning the mixture to obtain data for use in monitoring changes in the spectroscopic profile of the mixture as mixing proceeds, the monitoring means being in the form of a self-contained unit mounted releasably on the vessel.

According to a third aspect of the present invention there is provided apparatus for mixing a number of components (for example to produce a homogeneous mixture), comprising a vessel for receiving the components, drive means for rotating or oscillating the vessel about an axis to effect mixing of the components within the vessel, and at least one spectroscopic monitoring means provided directly or indirectly on-board the vessel for repeatedly scanning the mixture to obtain data for use in monitoring changes in the spectroscopic profile of the mixture as mixing proceeds, the monitoring means including means for radiatively transmitting to an off-board receiver an output for use in controlling the mixing process.

According to another aspect of the invention there is provided apparatus for mixing a number of components (for example, to produce a homogeneous mixture), comprising a mixing zone for receiving the components, means for mixing of the components within the mixing zone, and at least one spectroscopic monitoring means for repeatedly scanning the mixture within and/or downstream of the mixing zone to obtain and record data for use in monitoring changes in the spectroscopic profile of the mixture as mixing proceeds, means responsive to the monitoring means for modifying, e.g. terminating, the mixing process when the spectroscopic data obtained signifies attainment of a desired level of mixing and data acquisition means for collecting recorded data from the monitoring means, the data acquisition means having a docking station with which the monitoring means can be docked on completion of the mixing process to allow transfer of recorded data from the monitoring means to the data acquisition means.

To facilitate docking the monitoring means is preferably in the form of a portable unit, e.g. hand portable, adapted for detachable mounting on a wall of the mixing zone so that, on completion of the mixing cycle, the monitoring means can be dismounted and transported, e.g. manually, to the docking station. For the purposes of portability, the unit incorporating the monitoring means will usually conform with HSE Manual Handling Operations Regulations 1992 and will typically be no more than 25 kg in weight, preferably less.

A guide rail or rails may be provided on the vessel for locating the unit in a desired position, e.g. with the monitoring means properly registered with the window, so that the unit may be initially be engaged with the guide rail(s) and then adjusted by sliding the same along the rail(s) to the desired position before securing it in that position with the aid of releasable fastening devices.

The docking arrangement may include one or more hook formations on the unit and a support or supports on the vessel so that the unit can be offered up to the vessel by hooking the hook formation(s) to the support(s) which may comprise a rail to permit sliding adjustment of the unit after engaging the hooks with the rail. In this way, the unit may be temporarily suspended from the support(s) to free the hands of the operator and thereby allow him to operate a fastening device or devices to secure the unit in place so that the unit is held in place by the hook formation(s)/support and the fastening device(s).

The monitoring means may be provided with one or more handles to aid manipulation during detachment from the wall of the mixing zone, docking with the data acquisition means and/or transport between the mixing zone and the data acquisition means.

The rotatable or oscillatable mixing vessel may comprise a so-called V-blender of the type described in EP-A-0631810, the relevant disclosure of which is incorporated herein by this reference.

Alternatively, and more preferably, the rotatable or oscillatable mixing vessel may comprise a so-called Intermediate Bulk Container (IBC) designed for use in conjunction with an installation comprising a drive unit and a mounting frame for receiving and supporting the IBC, the mounting frame being coupled with the drive unit for rotation about an axis to effect tumbling of the components within the IBC as the latter rotates with the mounting frame.

In accordance with another aspect of the present invention there is provided an IBC provided with a window allowing for the scanning of the contents thereof by spectroscopic monitoring means, preferably near infrared spectroscopic monitoring means.

In accordance with a further aspect of the invention there is provided an IBC provided with docking means for the releasable mounting of a spectroscopic monitoring means for the scanning of the contents of the IBC.

Also in accordance with the invention there is provided an IBC provided with a spectroscopic monitoring means for the scanning of the contents of the IBC, the monitoring means preferably being non-invasively mounted on the IBC in registry with a window through which the scanning radiation is transmitted.

Usually the IBC is in the form of a hopper, typically of generally rectangular cross-section, with an inlet for components to be mixed at a large cross-section upper part of the IBC and an outlet for discharge of the mixture at a somewhat smaller cross-sectional lower part.

The IBC may be provided with means for coupling the same to a drive unit for rotating or oscillating the IBC, usually about an axis which extends obliquely with respect to the IBC, e.g. such that the axis of rotation or oscillation does not intersect the axis about which the IBC is generally symmetrical.

The IBC is conveniently transportable; for instance, it may be provided with ground-engaging wheels or may be adapted for mounting on a wheeled vehicle such as a trolley.

The coupling between the IBC and the drive unit may be through the agency of a mounting frame associated with the IBC or the drive unit.

Where the mounting frame is associated with the drive unit, the frame may comprise upper and lower sections which are relatively movable towards and away from one another between a loading position in which the IBC may be introduced into the mounting frame and a clamping position in which the IBC is raised out of contact with the ground and securely clamped for rotation with the frame.

The frame may be supported from a shaft of the drive unit for rotation about an axis which is obliquely orientated with respect to a central axis of the frame whereby the IBC and its contents are rotated an axis which is oblique with respect to the axes about which the IBC is generally symmetrical. The axis of rotation for instance may be substantially horizontal and the mounting frame may have a generally horizontal axis about which it is substantially symmetrical and which is inclined in a horizontal plane with respect to the rotational axis of the drive means, e.g. at an angle which may range from about 10° to about 40°, with 17° and 30° being typical angles of obliqueness.

While the monitoring means is preferably provided directly on the IBC, we do not exclude the possibility that the monitoring means may be provided on the mounting frame and arranged to effect monitoring the contents of the IBC, e.g. through a strategically located window provided in a wall of the IBC.

According to a further aspect of the present invention there is provided apparatus for mixing a number of components (for example to produce a homogeneous mixture), comprising a housing having an inlet and an outlet for receiving the components and means for effecting feed of the components from the inlet to the outlet while effecting mixing thereof, means for feeding the components to the inlet while mixing is taking place and means for collecting the mixture from the outlet while mixing is taking place, the housing being provided with at least one near infrared spectroscopic monitoring means for repeatedly scanning the mixture within the mixing zone and/or downstream thereof to obtain data for use in monitoring changes in the spectroscopic profile of the mixture.

The monitoring means may be arranged to scan the mixture in the mixing zone and/or a point downstream of the outlet, e.g. in a conduit connected to receive the mixed components from the mixing zone.

In this last-mentioned aspect of the invention, the monitoring means may be deployed to scan the mixture at a location along the path of travel through the housing and/or downstream of the outlet where the mixture would normally be expected to be in the desired state, e.g. substantially homogeneous, and comparison means may be provided for comparing the scanned spectroscopic profile of the mixture with previously obtained scanned profiles or with a predetermined target profile representing the desired state, e.g. homogeneous end point, for the mixture. In this way, if the comparison indicates that the mixture has not attained the desired state, the mixing process can be modified or terminated to allow remedial action to be taken.

In one embodiment of the invention according to this aspect of the invention, the mixing zone is within a stationary housing and mixing is effected by means of a rotatable or angulary oscillatable mixing device which also serves to feed the mixture of components towards the outlet.

The monitoring means employed in the present invention is preferably a near infra red spectroscopic unit having a solid state tunable filter, such as an acoustic-optic tunable filter.

The invention also resides in a method of mixing including, inter alia, the following aspects considered individually or, where the context admits, in combination with each other and/or in combination with aspects and features of the invention referred to above:

A method of mixing a number of components (for example to produce a substantially homogeneous mixture thereof) comprising introducing the components into a mixing vessel, rotating or oscillating the mixing vessel to effect mixing of the components and non-invasively monitoring mixing by collecting spectroscopic data from the mixture during rotation or oscillation of the vessel.

A method of mixing a number of components (for example to produce a substantially homogeneous mixture thereof) comprising introducing the components into a mixing vessel, rotating or oscillating the mixing vessel to effect mixing of the components, monitoring mixing by collecting and optionally analysing spectroscopic data from the mixture by means of spectroscopic monitoring means which rotates or oscillates with the vessel.

A method of mixing a number of components (for example to produce a substantially homogeneous mixture thereof) comprising introducing the components into a mixing vessel which has an axis about which it is substantially symmetrical, rotating or oscillating the mixing vessel about an axis which extends obliquely relative to said vessel axis to effect mixing of the components and monitoring mixing by collecting spectroscopic data from the mixture during rotation or oscillation of the vessel.

A method of mixing a number of components (for example to produce a substantially homogeneous mixture thereof) comprising introducing the components into an IBC, rotating or oscillating the IBC to effect mixing of the components and monitoring mixing by collecting spectroscopic data from the mixture.

A method of mixing a number of components (for example to produce a substantially homogeneous mixture thereof) comprising introducing at least one of the components into a mixing zone, in a first phase of operation effecting mixing while monitoring the condition of said at least one component by collecting spectroscopic data representative of such condition, on detection that said at least one component has attained a desired condition adding at least one additional component to the mixing zone and, in a second phase of operation, effecting mixing while monitoring the condition of the mixture as supplemented with said additional component by collecting spectroscopic data representative of such condition to determine the attainment of a desired condition of said supplemented mixture.

The above aspect of the invention may be carried out in a rotating or oscillating vessel or it may be carried in a non-rotating vessel or conduit provided with mixing means such as a bladed rotor or an orbiting screw mixer. In the case of a non-rotating vessel or conduit, the material may be fed continuously through the mixing zone and the additional component or components may be introduced at one or more locations downstream of the point of introduction of said at least one component.

A method of mixing a number of components (for example to produce a substantially homogeneous mixture thereof) comprising introducing at least one of the components into a mixing vessel, in a first phase of operation rotating or oscillating the vessel while monitoring the condition of said at least one component by collecting spectroscopic data representative of such condition, on detection that said at least one component has attained a desired condition adding at least one additional component to the mixing vessel and, in a second phase of operation, rotating or oscillating the vessel while monitoring the condition of the mixture as supplemented with said additional component by collecting spectroscopic data representative of such condition to determine the attainment of a desired condition of said supplemented mixture.

A typical application lies in mixing pharmaceutical components where one of the components comprises a lubricant such as magnesium stearate. Care has to be exercised in ensuring that the lubricant does not fully coat the particles of said pharmaceutical components (sometimes referred to as overblending) otherwise subsequent tabletting of the mixture is not possible. Thus, in the last two mentioned aspects of the invention, the first phase may comprise partial blending of the pharmaceutical components in the absence of the lubricant component, while the second phase may comprise-addition of the lubricant component and completion of blending with the excipients and active to a desired level of homogeneity (but without overblending).

In the foregoing, two phases of mixing while collecting spectroscopic data are mentioned but it will be appreciated that there may be more than two such phases. For instance, there may be a further phase or phases in which a further component or components are added and mixing continued while collecting spectroscopic data allowing the attainment of the desired condition to be determined.

The condition monitored in the first phase may be of the same nature as that for monitored during the second stage. For example, in both phases, the condition monitored may be related to the level of homogeneity attained, i.e. substantially fully homogeneous or an acceptable level lying between for instance the fully inhomogeneous and the fully homogeneous states.

However, the conditions monitored need not be of the same nature. For instance, in the first phase, the components introduced may be in the form of fines and coarser particles and the first phase may comprise monitoring the extent of distribution of fines within the mass of coarse particles while the second phase, after introduction of the additional component(s), may involve monitoring for the attainment of the homogeneous endpoint or some other acceptable level of blending.

It will be appreciated that, where the context admits, the various method aspects of the invention may be carried out using the various aspects and features of the apparatus and/or IBC as described above. In particular, the method of the invention in its various aspects is preferably carried out using an acoustic optic tunable filter (preferably one based on a tellurium dioxide crystal) to produce, from a broad band radiation source (preferably a near infra red source), radiation at a wider range of different wavelengths or within different bands.

The invention will now be described by way of example only with reference to the accompanying drawings, in which:

FIG. 1 is a diagrammatic view of a so-called V-blender and an associated blending process arrangement;

FIG. 2 is a block diagram of a spectroscopic monitoring unit forming part of the apparatus of FIG. 1;

FIG. 2A is a diagrammatic view showing docking of the monitoring unit with a data acquisition and analysis unit;

FIG. 3 is a diagrammatic view of a continuously operable blender provided with a spectroscopic monitoring unit;

FIG. 4 is a diagrammatic view of a IBC;

FIG. 5 is a diagrammatic side view illustrating the loading position of a frame for mounting the IBC;

FIG. 6 is a similar view to that of FIG. 5 but showing the IBC is the raised, secured position in preparation for rotation and mixing of the IBC contents;

Figure 7:
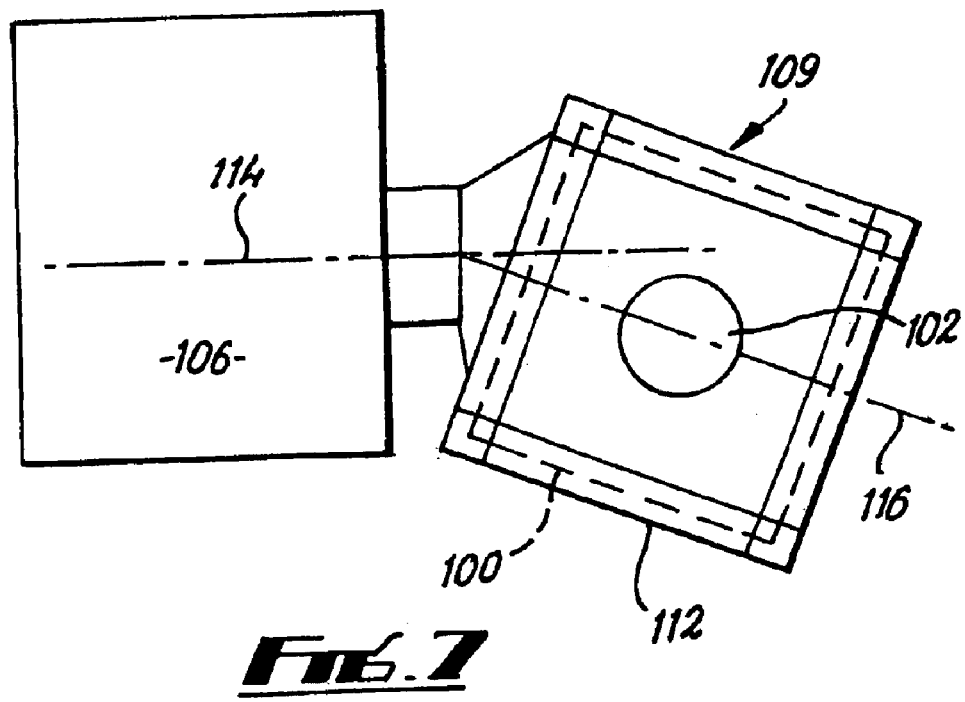
FIG. 7 is a diagrammatic plan view showing the orientation of the mounting frame and the IBC.

Referring to FIG. 1, blending of powders such as pharmaceutical actives and excipients is carried out in a V-blender. The design and operation of such blenders is well-known to those skilled in the art (for example, see EP-A-0631810). Briefly the V-blender comprises a vessel 10 which is generally V-shaped with two legs 12 and access openings 14 and 16 respectively located at the intersection between the legs and at the free ends of the legs 12. The openings 14, 16 allow the introduction of the components to be blended and their subsequent removal, each opening being provided with a closure member which is secured in place by suitable releasable fasteners (not shown). The vessel is mounted for rotation about an axis 18 which passes through the interior of the vessel. Thus, as shown, the vessel is provided with co-axial shafts 20 located on opposite sides of the vessel. The shafts are supported in suitable journals 22 and are coupled to the vessel in such a way that the shaft couplings are non-invasive, i.e. they do not project into the interior of the vessel and thereby potentially interfere with the blending process. One of the shafts is coupled to drive means 24 which typically comprises an electric motor and drive transmission means.

At a suitably strategic position, the vessel is provided with a window 26, the interior surface of which is substantially flush with the interior surface of the vessel walls so as to be non-invasive. At this location, a spectroscopic monitoring unit M is mounted on-board the vessel. The window location is selected so that scanning of the mixture of components at that location will provide representative spectroscopic profiles of the overall state of blending attained during the blending process. The window may of any suitable material compatible with transmitting the radiation without distortion; for example, in the case of near infrared radiation, the window may be of sapphire.

The monitoring unit in this embodiment houses a mixture scanning transducer 28 which under the control of control circuitry 30 generates radiation, e.g. near infrared radiation, for transmission into the vessel via the window 26 and receives radiation reflected back by the mixture of components immediately adjacent the interior surface of the window. Data corresponding to the reflected signal is stored in data storage means, e.g. a solid state data storage device (such as a RAM chip), forming part of computing means 34 which is programmed to analyse the data to derive, for each scan, a spectroscopic profile and may for example compare the scanned profile with a preloaded target profile representing the homogeneous end-point for the mixture of components undergoing blending. Scanning of the mixture is carried out repeatedly throughout the blending operation and the data collected during each scan is retained in the storage device. For instance, scanning may be carried out so as to obtain at least one spectroscopic profile per revolution of the vessel; typically in practice, hundreds or even in excess of one thousand such spectroscopic profiles may be obtained during each revolution. The mixing vessel typically rotates at a rate of about 7 to 8 rpm The monitoring unit M may continuously collect data through each revolution of the vessel. Some of the data collected of course may not be relevant since there will be periods of time during each revolution when the material is not present, or at least not present in a suitably packed form, immediately adjacent the viewing window. Nevertheless, this data may be collected and stored but can be identified, by virtue of the corresponding spectroscopic profile, as being of no relevance to the state of blending actually prevailing. At other times during the rotational cycle, the material will be resident at the window in a packed condition suitable for determination of the state of blending. The extent of packing may vary to some extent but sensitivity of the monitoring means to this variation may be controlled by appropriate selection of the wavelengths used in scanning.

The computing means 34 may store a number of target profiles each corresponding to a different set of components, or proportions, to be blended and is provided with user-input means (e.g. a dial, numeric keyboard or the like—not shown) by means of which the target profile appropriate for a given blending operation can be selected for the purpose of comparison with the scanned profiles. Instead of assessing the degree of mixing by reference to a predetermined target profile or profiles, the computing means may monitor changes in the data derived by scanning in order to identify convergence of the data towards a substantially static condition which may be equated with a desired degree of mixing. Thus, for example, the computing means may be programmed to average the data derived from a predetermined set of scans and determine the extent to which the averages are moving from one set of scans to the next so that once the average values converge and no longer fluctuate by more than a predetermined amount, this may be taken to represent a static condition corresponding to a desired state of mixing.

In practice, for the reasons mentioned above, the spectroscopic profiles obtained from each scan can vary substantially depending on the orientation of the vessel, i.e. some scans may correspond to a full view of the powder components while other scans may correspond to viewing free space. The computing means is therefore programmed to differentiate between "good" scans representative of the degree of mixing prevailing and "free space" scans. This may for instance involve comparing reflectance values at one or more wavelengths with a predetermined threshold value or values and rejecting those spectra with reflectance values less than the threshold value(s) and/or supplying the computing means with data signals indicating the rotational orientation of the vessel at one or more points in its cycle of rotation (or oscillation).

The spectroscopic technique employed may be near infrared spectroscopy preferably operating over the frequency range from 900 to 2500 nm. However, the invention is not limited to use of the near infrared region and other forms of spectroscopic device operating in the region of electromagnetic radiation wavelengths may be used such as an ultraviolet-visible spectrophotometer, a mid-range infrared spectrophotometer, an infrared spectrophotometer or a Raman spectrophotometer.

The unit M also includes a signal transmitter 36 for producing an output signal when the result of the profile comparison made by the computing means 34 establishes that the scanned profile matches the target profile, or is at least an acceptable match within predefined tolerances programmed into the computer means. The output signal so emitted may be a visual and/or audible signal for alerting an operator to the fact that the desired degree of mixing, e.g. the homogeneous end point, has been attained so that the operator can then terminate the blending cycle by switching off the drive motor. The signal transmitter 36 may in this instance be provided with a light source for producing a visual output, e.g. a flashing output, and/or a sound source such as a speaker for emitting an audible signal.

Alternatively the output signal may be used to terminate, or initiate termination of, the blending cycle automatically. In this case, the signal transmitter 36 may emit electromagnetic signals (e.g. radio frequency signals) for reception by a receiver forming part of control circuitry 38 associated with the drive means 24 so that, on receipt of the "matched" signal from the transmitter 36, the blending vessel can be brought to rest by shutting down the drive means.

The signals produced by the signal transmitter are preferably capable of being discriminated from the signals emitted by similar signal transmitters associated with other blenders/monitoring units M in the vicinity. Where the signals are radiatively transmitted, such discrimination may be by way of the frequency of transmission or the signals from different transmitters may be encoded differently from one another. Where the signals are in visual and/or audible form, discrimination may be achieved by using different colours, flashing regimes, sound frequencies, sound spectra etc or even by electronically generated spoken output stating that a given blending vessel has completed its cycle (or wording to that effect).

The unit M is self-contained in that it collects and stores spectroscopic data from the vessel, makes a comparison between the scanned spectral profiles and the appropriate target profile. It is also self-powered, the power supply for the various components of the unit being in the form of one or more batteries (e.g. rechargeable batteries) accommodated by the unit M. Further, it may be sufficiently light and compact to be portable without the aid of mechanical handling equipment and for this purpose may be fitted with one or more handles H to facilitate carrying of the unit and mounting/dismounting operations of the unit relative to the blending vessel. The unit M may for instance comprise a common frame or base on which the various components are mounted.

The unit M is designed for rapid mounting and dismounting and, for this purpose, is provided with one or more releasable devices, by means of which the unit M can be secured to the vessel in defined orientation relative to the window 26, e.g. with the frame or base clamped to the vessel at a predefined docking location on the vessel. For instance, the unit may be provided with one or more latching members 29, e.g. Southco sprung draw latches, for co-operation with one or more corresponding keepers provided on the vessel (or vice versa), e.g. so arranged that the unit M has to be offered up to the vessel in a certain orientation in order to effect correct docking with the latch/latches and keeper/keepers correctly aligned for securing action. It will be noted that the unit M is mounted off-axis relative to the axis of rotation of the blender and that the spectroscopic scanning is effected non-invasively.

All of the data collected by the data storage device of the computing means 34 during a blending cycle is potentially of use for example in analysing the performance of the blender and the unit M. On completion of the blending cycle, the collected data is transferred to an electronic data acquisition and analysis unit (DAAU, not shown). The DAAU may be equipped with a defined docking location of similar design to that on the vessel so that fastening devices provided on the unit M may be used to secure the unit M to the DAAU during data transfer. The DAAU may include means for relating the transferred data with for example the particular blender, the monitoring unit M used and/or the blending cycle performed; for instance, the DAAU may include input means, e.g a keyboard or the like, for such identification data. Once data transfer to the DAAU has been effected, the scanning-derived data stored in the unit M from the relevant blending cycle may be deleted or overwritten in a subsequent blending cycle.

The unit M also includes a compartment for a power supply 40, e.g. in the form of a rechargeable battery or batteries. The power supply 40 may be maintained fully effective by removing the rechargeable battery or batteries during the downtime between successive blending operations and substituting a fully charged battery or batteries, the replaced batteries then being put on recharge in readiness for insertion into the same unit or another monitoring unit once fully recharged.

In the embodiment described with reference to FIGS. 1 and 2 (and also those described hereinafter) analaysis of the scanned data, e.g. comparison of the scanned profiles with a target profile, is carried out on-board and the signal to terminate the blending operation is emitted by the on-board transmitter. Various modifications are possible, including for example "off-board" data storage and/or data analysis, e.g. comparison of scanned and target profiles, during the blending cycle. For instance, the data obtained by repeated scanning may be transferred from the unit M to a separate "off-board" computing means having a data storage facility and programmed to analyse the data in order to determine the attainment of a desired degree of blending. Data transfer from the unit M to the computing means may in this case be effected by radiative transmission from the transmitter 36, e.g. by way of radio frequency signal coded with the data undergoing transfer, to a receiver associated with the computing means. In such embodiments, control of the drive means for the blending vessel may be effected by signals derived from the computing means, e.g. representing "matching" of the scanned and target profiles, and such signals may be transferred to the control circuitry 38 associated with the drive means either through radiative transmission using a transmitter-receiver pair or by a hard-wired connection.

Also while FIGS. 1 and 2 illustrate the use of a single monitoring unit M, it will be appreciated that each blender may be equipped with more than one on-board monitoring unit and window combination located at different strategic locations on the vessel. Moreover, instead of the monitoring unit or units M being battery powered, we do not exclude the possibility of powering the same from a separate off-board electrical power source (e.g. the mains supply) via cabling which may be coupled to an on-board monitoring unit via slip rings or other couplings allowing electrical connections to be made to the monitoring unit when mounted on the rotating or oscillating vessel.

Referring now to FIG. 3, this illustrates an embodiment of the invention in which blending or mixing of the components is effected on a continuous rather than a batch basis within a passageway defined by a housing 50 having an inlet 52 for introduction of the components to be blended and an outlet 54 of removal of the blended mixture. The blending process is continuous in this embodiment in the sense that components are being fed to the blender and homogeneously blended mixture removed therefrom while blending is taking place within the housing 50. Mixing is effected by a shaft mounted agitator 55 (e.g. an auger-type device) which can rotate or oscillate angularly about the shaft axis to tumble and mix the components while advancing them from the inlet to the outlet. A window 56 (e.g. a sapphire window) is strategically located on the housing at a point along the path of travel of the mixture where the components have undergone sufficient mixing that the homogeneous end point will normally have been attained or is sufficiently close that homogeneity will inevitably occur as the mixture travels through the remainder of the housing.

The housing 50 is provided with a monitoring unit M which may be substantially as described with reference to FIGS. 1 and 2 and may be coupled to the housing 50 at a docking location including the window 56 so that spectroscopic data can be collected for analysis, for instance using the techniques referred to above in relation to the embodiment of FIGS. 1 and 2. In this case the analysis, e.g. comparison between the scanned and target profiles, is used as a check to ensure that the desired level of homogeneity is being secured during the continuous blending of the components. If the comparison reveals that the scanned profiles are not sufficiently matched with the target profile, the monitoring unit M is operable to produce a signal either to alert an operator to the fact that inadequate blending is occurring or to terminate the blending process, i.e. as described above in relation to FIGS. 1 and 2. Again the monitoring unit M will be portable and attachable to the housing 50 by a quick release device or devices. Also, it may be designed for docking with a data acquisition and analysis unit as described previously.

In the embodiment of FIG. 3, the monitoring unit M is not mounted on a rotating part of the blending equipment. Consequently, transmission of signals from the unit M may be more readily be effected by way of hard-wired connections, although we do not exclude the possibility of radiative transmission. Also while this embodiment illustrates a housing 50 which comprises a conduit in which the mixer rotates about a fixed axis generally concentric with the axis of the housing, in a modification, the housing may be generally hopper-shaped and the mixer may be an orbiting screw mixer.

The spectroscopic monitoring unit M as used in the embodiments described above and hereinafter may include a solid state tellurium dioxide non-collinear acoustic-optic tunable filter of the type disclosed in the article "Acoustic-Optic Tunable Filters Spectrally Modulate Light" by Dr Xiaolu Wang and published in the August 1994 edition of Laser Focus World (the entire disclosure of which is incorporated herein by this reference). As described in that article, the filter may be associated with a tungsten lamp to provide a fast tuning near infrared source for spectroscopic applications. The detector used may be In—Ga—As detector. A suitable form of spectroscopic monitoring unit for use in the present invention is the Luminar 3030-701-INT AOTF-NIR Free Space Spectrometer, wavelength range 1100 to 2300 nm (and also the corresponding 2030 model, wavelength range 900 to 2300 nm) commercially available from Brimrose Corporation of Baltimore, Md. 21236, USA. Another device that may be employed in embodiments of the present invention is the NIR Optical Spectrograph Card (NIROSC), including an In—Ga—As diode array, available from Control Development Corporation of Indiana, USA.

Various other forms of spectroscopic unit may be used. The radiation source may be a broad spectrum visible to infra-red source, such as a tungsten-halogen lamp, which emits radiation in the near infra-red interval of from 400 to 2500 nm. While it is preferred that the filter arrangement is constituted by an AOTF as mentioned above, the filter arrangement may comprise a plurality of filters each allowing the passage of radiation of a respective single frequency or frequency band. In other embodiments the radiation source could be any of a source of visible light, such as an arc lamp, a source of x-rays, a laser, such as a diode laser, or a light-emitting diode (LED) and the filter arrangement could be replaced by a diffraction grating, a monochromator or a spectrometer of Fourier transform kind.

The detector may be an integrating detector, such as an Si, PbS or In—Ga—As integrating detector, a diode array detector, such as an Si or In—Ga—As diode array detector, or a one or two-dimensional array detector, such as a CMOS chip, a CCD chip or a focal plane array. In use, the detector will produce signals depending upon the composition of the mixed material and the frequency of the provided radiation.

Referring now to FIGS. 4 and 5, a particularly convenient implementation of the invention is possible using a so-called IBC and drive installation for mounting and for rotating the IBC. Such installations are commercially available from Matcon U.K. of Gloucestershire, UK. The IBC comprises a hopper-shaped vessel 100 having an inlet port 102 at its upper larger cross-sectional part and an outlet 104 at its lower cross-sectional part. Components to be mixed are introduced into the IBC through the inlet port and the mixture is discharged through the outlet port 104 which may be equipped with means (not shown) for facilitating such discharge. Such means may for instance comprise Matcon cone valve technology . The inlet and outlet ports are provided with closure means (not shown). The IBC is generally symmetrical about its vertical axis with a larger cross-section upper part and a lower part having a progressively reducing cross-section towards the outlet 104, i.e. as a result of its hopper configuration. The IBC is typically of rectangular cross-section in the horizontal plane The IBC is adapted to be mounted on a drive unit 106 having a drive shaft 108 to which an IBC mounting frame 109 is coupled. The frame 109 comprises upper and lower frame parts 110, 112 which are relatively movable towards and away from each other (e.g. the lower frame 112 may be movable and the upper frame 110 may be fixed) between an IBC loading position as illustrated in FIG. 5 and an IBC supporting position as illustrated in FIG. 6 in which the IBC is raised out clear of the ground and is securely clamped for rotation with the frame 109. As shown in the plan view of FIG. 7, the frame 109 is mounted on the drive shaft 108 in such a way the generally vertical plane of symmetry of the frame is obliquely inclined relative to the rotation axis 114 of the shaft 108. Likewise when the IBC is mounted in the frame as shown in FIG. 6, the horizontal axis 116 about which the IBC is generally symmetrical extends obliquely relative to the rotation axis 114. In operation, the obliquely mounted IBC is rotated about the axis 114 to effect mixing of its contents.

The IBC is equipped with a monitoring unit M which is coupled to a strategically located docking station on the IBC, e.g. on one of the inclined side walls thereof. The unit M is generally of the same design as and may have all of the characteristics as described in relation to the unit M of FIGS. 1 and 2 and, when docked, will be in registry with a window (not shown) in the side wall so that scanning of the contents of the IBC can be effected during the mixing process. The monitoring unit M may for example comprise a Brimrose battery-powered spectroscope AOTF unit as referred to above. As in the embodiment of FIG. 2, the monitoring unit M may be designed to control the mixing cycle, e.g. by production of a signal which is transmitted to an off-board receiver and associated signal utilising means which controls the drive unit 106. Thus, for instance, when the spectroscopic data collected by the monitoring unit M indicates that the mixture has progressed to a desired condition, e.g. the homogeneous endpoint for the mixture, the monitoring unit may emit a signal which triggers operation of the drive unit 106 to terminate rotation of the frame 109 and position the IBC in the configuration shown in FIG. 6 to allow the contents of the IBC to be discharged for transfer to further processing means, e.g. tableting equipment.

Alternatively, after rotation has been terminated, the IBC may be unloaded from the frame with its contents intact and then transferred to another processing stage. Another alternative involves restoring the IBC to the FIG. 6 configuration and then adding a further component or components to the IBC for mixing with the resident material in the IBC by further operation of the drive unit 106, again using the monitoring unit to monitor the mixing operation as described above. The mixing procedure may involve supplementing the resident material in the IBC with additional components in one or more stages, the IBC contents being monitored during each such stage and mixing being suspended on attainment of the desired mixing conditions (as detected by the monitoring means) during each stage while an additional component or components are added. Once all components have been added and mixed to the desired condition, the IBC is restored to the FIG. 6 configuration for discharge of its contents or for removal (after lowering into the FIG. 5 position) and transfer to a further processing stage.

The staged mixing of components as described above may also be carried out in the embodiment of FIGS. 1 and 2 and that of FIG. 3. In the case of FIG. 3, the further component or components may be introduced at different points along the length of the housing 50.

Although it is preferred to carry out monitoring non-invasively, i.e. without encroaching or interfering with the mixing process within the mixing vessel, we do not exclude the possibility of monitoring unit designs which are invasive.

Figure 8:
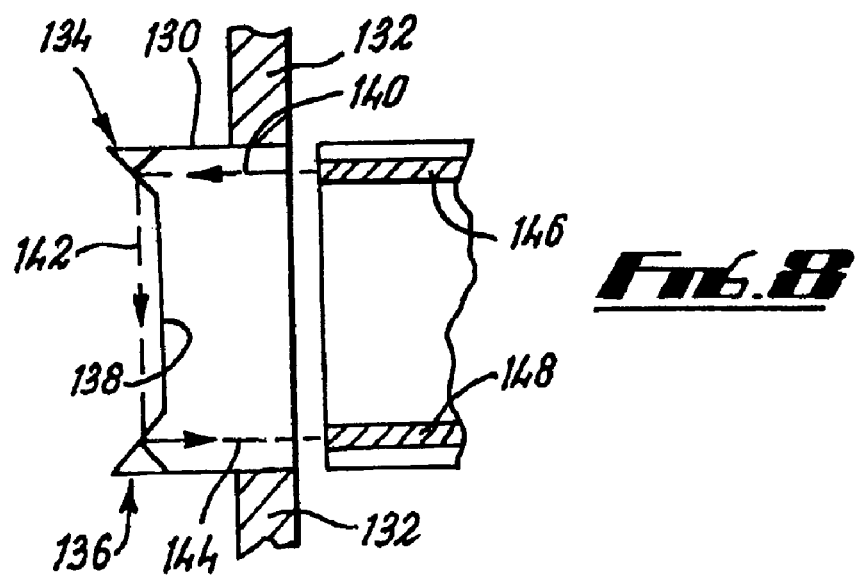
FIG. 8 is a diagrammatic view of a probe arrangement for transmission scanning of the mixing zone.

The mode of scanning is by diffuse reflection of the monitoring radiation. However, it will be appreciated that other scanning modes may be used, such as reflectance techniques in which the radiation is transmitted to a reflective surface located within the mixing zone and the reflected radiation is detected by the spectroscopic monitoring unit, or a technique in which the radiation is transmitted from one location and detection of the radiation is effected at a different location. One embodiment utilising the latter technique is illustrated in FIG. 8 in which the radiation is routed through the interior of the mixing vessel by means of a probe 130 which projects into the vessel through wall 132. The probe is composed of material suitable for transmission of the radiation employed and, by means of reflective surfaces 134, 136 and recessed end face 138, defines a transmission path comprising an entry path 140, a interactive path 142 extending through the recess in the end face and hence through the interior of the mixing zone, and a return path 144. The radiation is directed to the probe 130 from the AOTF or equivalent by optical fibre means 146 and is returned to the detector of the monitoring means by optical fibre means 148, the optical fibre means 146, 148 being provided on a support forming part of the monitoring means and which is brought into registration with the probe 130 on mounting of the monitoring means on the vessel.

Figure 9:
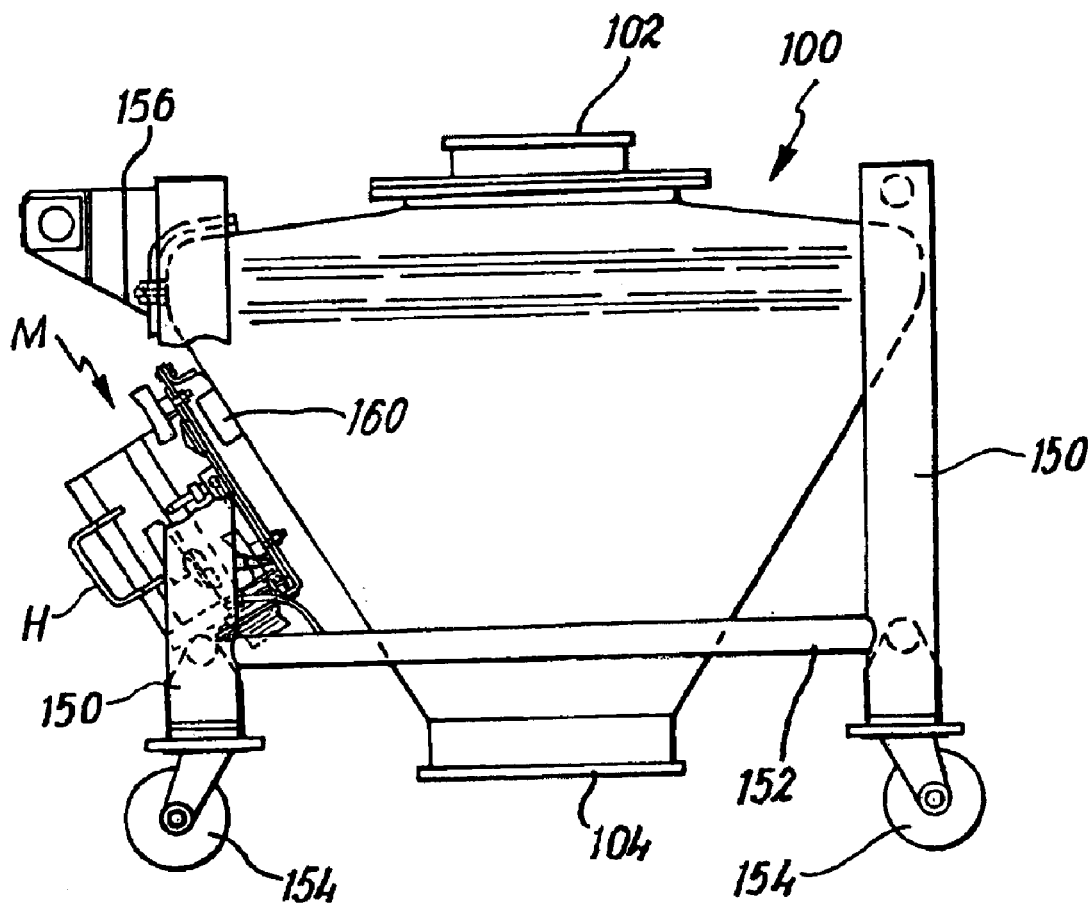
FIG. 9 is a front elevational view of an integrated framework and IBC arrangement with part of one of the uprights broken away to afford a view of the viewing window provided on the IBC.
Figure 10A:
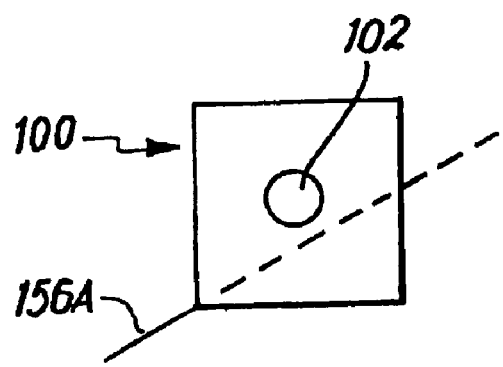
FIG. 10A is a diagrammatic plan view showing the axis about which the IBC is rotated.
Figure 10:
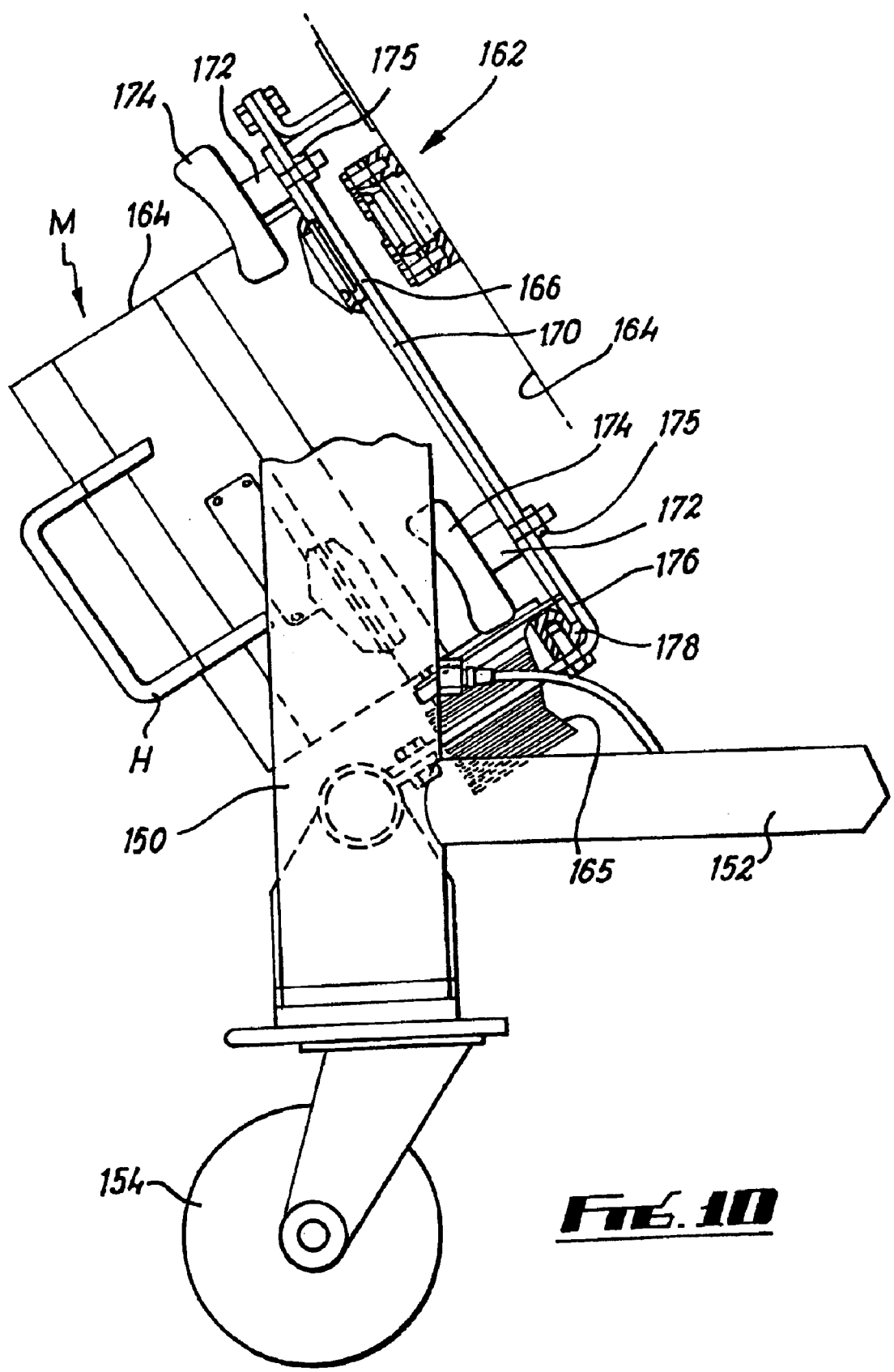
FIG. 10 is an enlarged view of that part of the IBC provided with means for docking of the monitoring means.

In the embodiment of FIGS. 4 to 7, the IBC is illustrated diagrammatically. In practice, the IBC may be equipped with a framework to facilitate its handling, transport and coupling to the drive unit 106. Such an arrangement is illustrated in FIGS. 9 and 10 to which reference is now made. As shown, the framework comprises uprights 150 located at the four corners of the IBC 100 and interconnected by cross-members 152, the IBC being mounted within the framework with its outlet located in spaced relation to the floor level. The framework may be adapted for use with a fork lift to facilitate mounting on and dismounting from the drive unit 106. The lower ends of the uprights 150 are provided with swivelling ground-engaging wheels 154 to facilitate mobility. At one side, the upper part of the IBC framework is provided with a fitting 156 for coupling the IBC and its framework to the drive unit 106 in a substantially the same manner as illustrated in FIG. 7 so that, in operation, the IBC is rotated about an oblique axis 156A (see FIG. 10A) to secure an efficient tumbling action of its contents.

The monitoring unit M is mounted on one side of the IBC in registry with a viewing window 160 (e.g. a sapphire window) provided on the sloping wall 162 of the IBC to allow radiation transmission into the interior of the IBC. Mounting of the unit M is shown in more detail in FIG. 10. The unit M comprises a housing 164 provided with handles H facilitating handling of the unit and heat dissipating fins 165 or the like for removal of heat generated during operation of the unit. The housing accommodates the various components described above in connection with FIGS. 1 and 2, including for example a spectroscopic monitoring unit such as Luminar 3030 AOFT spectroscopic equipment. The housing includes a window 166 through which outbound and inbound radiation can pass and which, when the housing 164 is mounted on the IBC, registers with the window 160. To this end, the IBC and associated framework is provided with a mounting structure 168 to which the monitoring unit M can be releasably secured.

The unit M incudes a plate 170 in which the window 166 is provided which carries a number of releasable fastening devices 172 in the form of screwthreaded bolts which can be rotated by hand grips 174 and are intended to register with apertures in the mounting structure 168 for engagement with captive nuts 175. One edge 176 of the plate 170 forms a lip which inserts into a locating channel defined between the mounting structure 168 and a rebated member 178 secured to the mounting structure. The unit M is assembled to the mounting structure 168 by initially locating the lip 176 in the channel and, if necessary, positioning the unit M to register the fastening devices 172 with the associated apertures and nuts 175. The fastening devices are then operated to firmly clamp the unit M in place for rotation with the IBC and its associated framework.

Figure 11:
FIGS. 11 and 12 are graphs in 3 dimensions and 2 dimensions respectively illustrating convergence of spectroscopic profiles during the course of a mixing cycle.
Figure 12:
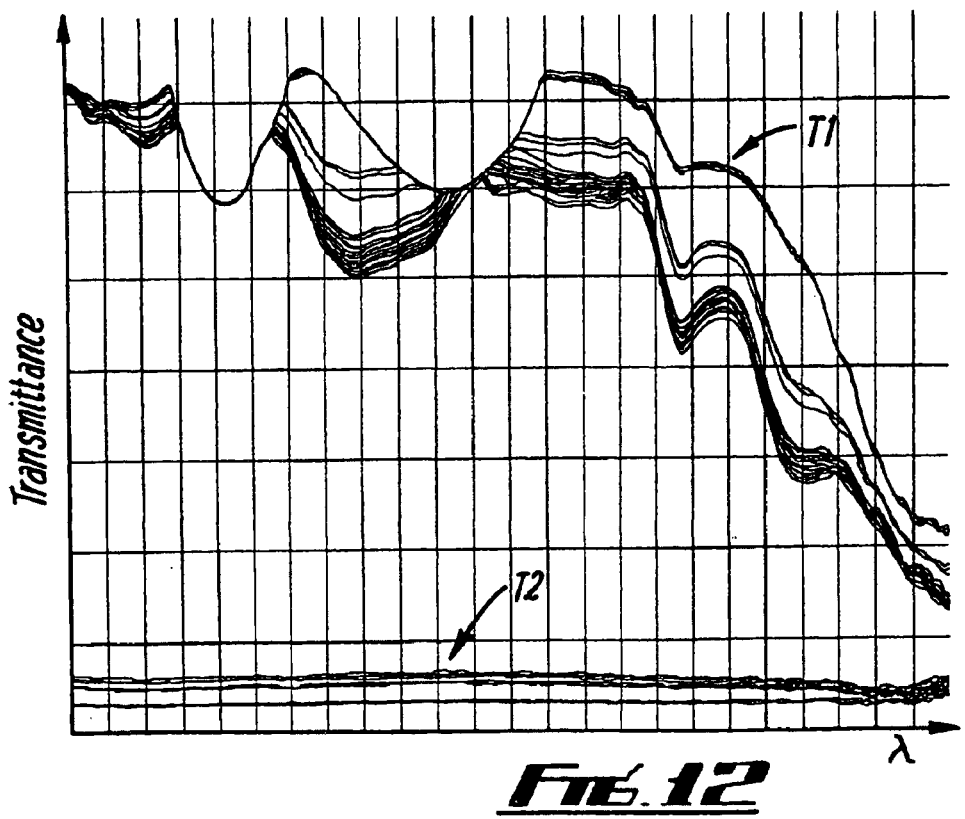

FIGS. 11 and 12 illustrate typical scans derived by the monitoring unit M during operation. FIG. 11 illustrates the time axis in the reverse direction with the more recent traces shown in the foreground. The traces T1 are scanned profiles which meet a predetermined criterion and are considered to be representative of the state of mixing, while traces T2 are scanned profiles which correspond to free space. In practice, the monitoring unit M may process other profiles (not illustrated) which do not correspond lie between the two sets of traces T1 and T2 but are views of free space and components of the mixture and hence are rejected along with traces T2. From FIG. 11, it will be seen that the traces T2 gradually converge towards a static, substantially unchanging profile which may be indicate that the mixture has reached a certain state of mixing, e.g. a homogeneous end point. In determining convergence, reference may be had to a specific part or parts of the spectroscopic profiles, e.g. one or more wavelengths or wavelength ranges corresponding to the nature of the materials being mixed. For instance, the profiles may be analysed for convergence in a wavelength region or regions which correspond to the hydrocarbon content of the components undergoing mixing.

In prior PCT Application No. PCT/SE99/01325 there is disclosed apparatus for and a method for mixing a plurality of materials to supply a mixture having a required homogeneity. The teachings in PCT Application No. PCT/SE99/01325 (the entire disclosure of which is incorporated herein by this reference) relating to the management of the feed of mixed material through a supply line are incorporated herein by this reference and are applicable for example to the management of the mixed components after exiting the mixing vessel.

Also, PCT/SE99/01325 describes the use of measuring devices for measuring on-line, at at least one point in a supply line, the composition of the mixture passing through the supply line. In accordance with a further aspect of the present invention, the apparatus and method disclosed in PCT Application No. PCT/SE99/01325 may be modified by employing measuring device(s) in the form of monitoring means as disclosed herein. Thus, for instance without being exhaustive, the measuring devices may each be in the form of a monitoring unit having one or more of the following features:

- detachable mounting as a unit (which may be self-powered and/or self-contained and/or portable) on the supply line;
- communication with signal utilising means controlling the material feed and/or data acquisition means may be through a transmitter/receiver arrangement using radiative transmission, such as radio frequency signals;
- generation of the scanning radiation with the aid of an OATF as described herein;
- collection and storage of data within the monitoring means, preferably using a solid state memory device;
- comparison of scanned profiles obtained at each location with a target profile stored locally within the monitoring unit, e.g. using solid state memory; and
- dockable with data acquisition and/or analysis means to allow data collected by the monitoring means to be transferred to the data acquisition and/or analysis means.

What is claimed is:

1. A method of mixing a plurality of components, comprising:
    a) introducing components into a mixing vessel;
    b) mixing said components by rotating or oscillating the mixing vessel;
    c) non-invasively monitoring the contents of the vessel during said mixing with a monitor that collects spectroscopic data, and
    d) storing said spectroscopic data on a data storage device, wherein said data storage device is mounted on said oscillating or rotating mixing vessel.

2. A method of mixing a plurality of components, comprising:
    a) introducing components into a mixing vessel;
    b) mixing said components by rotating or oscillating the mixing vessel; and
    c) monitoring the contents of the vessel during said mixing by means of a monitor which rotates or oscillates with the vessel.

3. The method of claim 2, wherein said monitor collects spectroscopic data.

4. The method of claim 3, further comprising storing said spectroscopic data on a data storage device.

5. The method of claim 4, wherein said data storage device is mounted on said oscillating or rotating mixing vessel.

6. The method of claim 5, further comprising transferring said data from the data storage device to a data acquisition device after rotation or oscillation of the vessel has been discontinued.

7. The method of claim 6, wherein, after rotation or oscillation of the vessel has been discontinued, the monitor is physically relocated to and docked with the data acquisition device.

8. The method of claim 3, including transferring the data from the monitor to an off-board data storage or a data acquisition device during the mixing process.

9. The method of claim 2, wherein said vessel is an Intermediate Bulk Container.

10. The method of claim 2, further comprising modifying said mixing in response to at least one signal.

11. The method of claim 10, wherein said modification comprises discontinuing rotation or oscillation of the vessel.

12. The method of claim 2, wherein said components include at least one pharmaceutical component.

13. The method of claim 2, wherein said components include at least one lubricant.

14. The method of claim 2, wherein said monitor comprises an acoustic optic tunable filter to produce, from a broad band radiation source, radiation at a wide range of different wavelengths and/or within different bands.

15. A method of mixing a plurality of components, comprising:
  a) introducing components into a mixing vessel;
  b) mixing said components by rotating or oscillating the mixing vessel; and
  c) monitoring the contents of the vessel during said mixing, wherein said mixing vessel has an axis of symmetry about which it is substantially symmetrical; and said mixing vessel is rotated or oscillated about an axis that extends obliquely relative to said axis of symmetry.

16. The method of claim 15, in which the vessel comprises an Intermediate Bulk Container (IBC).

17. A method as claimed in claim 15 comprising introducing the components into an Intermediate Bulk Container (IBC) which constitutes said mixing vessel, rotating or oscillating the IBC to effect mixing of the components and monitoring mixing by collecting spectroscopic data from the mixture.

18. A method of mixing a plurality of components, comprising:
  a) introducing at least one component into a mixing zone;
  b) mixing said at least one component, while monitoring at least one condition by collecting spectroscopic data, to form a mixture; and
  c) mixing in at least one additional component to said mixture while monitoring said at least one condition.

19. A method as claimed in claim 18 further comprising: mixing the at least one component within said vessel by rotating or oscillating the vessel, while monitoring a condition of said at least one component by collecting spectroscopic data representative of such condition; determining that said condition has attained a first desired value; adding said at least one additional component to the mixing vessel; further mixing the components within said vessel while collecting spectroscopic data; and determining that said condition has attained a second desired value.

20. The method of claim 19, wherein said at least one component comprises a pharmaceutical component, and wherein said at least one additional component comprises a lubricant component.

21. A method as claimed in claim 18 comprising: introducing said at least one component into the mixing zone and in a first phase of operation effecting mixing while monitoring the condition of said at least one component by collecting spectroscopic data representative of such condition; and on detection that said at least one component has attained a desired condition adding at least one additional component to the mixing zone and, in a second phase of operation, effecting mixing while monitoring the condition of the mixture as supplemented with said additional component by collecting spectroscopic data representative of such a condition to determine the attainment of a desired condition of said supplemented mixture.

22. A method as claimed in claim 21 in which the first phase comprises partial blending of components including at least one pharmaceutical component while the second phase involves the addition of a lubricant component.

23. A method as claimed in claim 18, comprising: introducing said at least one component into a mixing vessel providing said mixing zone and, in a first phase of operation rotating or oscillating the vessel while monitoring the condition of said at least one component by collecting spectroscopic data representative of such condition; and, on detection that said at least one component has attained a desired condition adding at least one additional component to the mixing vessel and, in a second phase of operation, rotating or oscillating the vessel while monitoring the condition of the mixture as supplemented with said additional component by collecting spectroscopic data representative of such condition to determine the attainment of a desired condition of said supplemented mixture.

24. An apparatus for mixing a plurality of components, comprising:
  a) a mixer;
  b) at least one spectroscopic monitor for repeatedly scanning the contents of the mixer to obtain and record data for use in monitoring changes in the spectroscopic profile;
  c) a control device in communication with said at least one spectroscopic monitor to control mixing; and
  d) a docking station for receiving said monitor and allowing transfer of data from the monitor to a data acquisition device.

25. The apparatus of claim 24, wherein the monitor is a portable unit adapted for detachable mounting on a wall of the mixer that, on completion of the mixing cycle, the monitor can be dismounted and transported to the docking station.

26. The apparatus of claim 25, wherein the mixer comprises at least one guide rail for mounting the portable unit in a desired position.

27. The apparatus of claim 24, wherein the monitor is provided with at least one handle.

28. Apparatus for mixing a number of components comprising a vessel for receiving the components, drive means for rotating or oscillating the vessel about an axis to effect mixing of the components within a vessel, and at least one spectroscopic monitoring means for repeatedly scanning the mixture to obtain data for use in monitoring changes in the spectroscopic profile of the mixture as mixing proceeds, the monitoring means being mounted off-axis relative to the axis about which the vessel is rotatable or oscillatable.

* * * * *